US006669654B2

United States Patent
Diokno et al.

(10) Patent No.: US 6,669,654 B2
(45) Date of Patent: Dec. 30, 2003

(54) METHOD FOR MEASURING POSITIONS AND DIMENSIONS OF VAGINAL PROLAPSES WITH A VAGINAL SPECULUM HAVING REMOVABLE BLADES

(76) Inventors: Ananias Diokno, 480 Hillspur Rd., Ann Arbor, MI (US) 48105; German Borodulin, 583 46th Ave., San Francisco, CA (US) 94121; Alexander Shkolnik, 485 Dartmouth Ave., San Carlos, CA (US) 94070

( * ) Notice: Subject to any disclaimer, the term of this patent is extended or adjusted under 35 U.S.C. 154(b) by 89 days.

(21) Appl. No.: 10/046,674

(22) Filed: Jan. 16, 2002

(65) Prior Publication Data
US 2002/0177791 A1 Nov. 28, 2002

Related U.S. Application Data (62) Division of application No. 09/565,613, filed on May 4, 2000, now Pat. No. 6,379,299.

(51) Int. Cl.[7] .............................................. A61B 5/103
(52) U.S. Cl. ...................................................... 600/591
(58) Field of Search ................................. 600/591, 593, 600/220, 222, 221, 223, 202, 184, 201, 215, 587

(56) References Cited

U.S. PATENT DOCUMENTS

| 2,579,849 | A | * | 12/1951 | Newman | 600/215 |
| 3,716,047 | A | * | 2/1973 | Moore et al. | 600/212 |
| 3,815,585 | A | * | 6/1974 | Fiore | 600/222 |
| 6,379,299 | B1 | * | 4/2002 | Borodulin et al. | 600/220 |
| 6,468,232 | B1 | * | 10/2002 | Ashton-Miller et al. | 600/591 |

* cited by examiner

Primary Examiner—Pedro Philogene (57) ABSTRACT

The method of the invention for measuring positions and dimensions of vaginal prolapses is carried out with the use of a vaginal speculum having at least one removable with a scale. Measurements are carried out by manipulating the pivotally connected parts and the removable blade by inserting the moveable blade into the vagina of a female patient until contact with the reference point, e.g., the top of the cervix, and reading the number on the scale for determining the distance L1 from the reference point to the top of the cervix. The speculum is then withdrawn in a direction away from the cervix and expanded by rotating the pivotal parts for exposing the wall of the vagina on the side of the completely removable blade for observation. The exposed prolapse is evaluated with regard to its severity. The removable blade is shifted to the tip of the prolapse, and the distance L2 from the reference point to the tip of the prolapse is determined with the use of the scale. Position of the prolapse is then determined by subtracting L2 from L1.

7 Claims, 8 Drawing Sheets

METHOD FOR MEASURING POSITIONS AND DIMENSIONS OF VAGINAL PROLAPSES WITH A VAGINAL SPECULUM HAVING REMOVABLE BLADES

REFERENCE TO RELATED CASE

This application is divisional from U.S. patent application Ser. No. 09/565,613 filed May 4, 2000 now U.S. Pat. No. 6,379,299 for which Notice of Allowance was granted.

FIELD OF THE INVENTION

The present invention relates to medical diagnostic instruments, in particular to a method for measuring positions and dimensions of vaginal prolapses with a vaginal speculum having removable blades.

BACKGROUND OF THE INVENTION

A vaginal speculum is a diagnostic instrument for dilating the opening of the vagina cavity in order that the interior may be more easily visible for observation. A vaginal speculum has two expandable blades, which are inserted into the vagina in a closed state and then expanded, or moved apart for dilating the vaginal cavity. In particular, a vaginal speculum is an indispensable instrument not only for gynecologists but also for primary care physicians, geriatricians, urologists, and nurse practitioners for urological examination of patients suffering from urinary incontinence in order to exclude the presence of vaginal prolapses, such as rectocele, cystocele, enterocele, and uterine prolapse. Vaginal prolapses of the aforementioned type are protrusions or herniation of the urethra or other pelvic organs into the vagina.

One typical vaginal speculum is described in U.S. Pat. No. 3,716,047. The instrument consists of three parts of molded non-toxic plastic materials, i.e., a fixed member, a movable member, and a sliding member. The sliding member is slidingly installed in the fixed member and pivotally supports the movable member so that the movable member can be rotated around the pivot at the proximal end of the fixed member. As a result, the distal ends of the movable and fixed members, which form expandable blades insertable into the vagina, can dilate the vagina cavity and thus allow internal vaginal observations. The members are made from a transparent plastic and the blades form a thin-wall circular or oval cross-section, which allows the observation.

A procedure of examination of a vagina with the use of a speculum involves movements of the speculum in an expanded, i.e., an outwardly diverging state in the direction towards or away from the uterus. This is necessary for diagnosing aforementioned vaginal prolapses. However, since the opening of the vagina has a circular muscle, which is more resistant to dilations than the vaginal cavity, the aforementioned withdrawal of the expanded speculum may cause in patient discomfort and painful sensations. This is because in the course of the withdrawal of the speculum the diameter of its portion at the vaginal opening is stretched by the speculum. Furthermore, the conventional vaginal specula do not have features for measuring the length of vagina and for testing and measuring the severity of the prolapses without completely removing the entire speculum. Normally, the physician disassembles the speculum and inserts only one of the blades for pressing on one wall of the vagina for exposing and observing the opposite wall. In case of prolapses, a separate ruler is used for measuring the length and position of the prolapse or prolapses. The procedure is then repeated for exposing the opposite wall of the vagina cavity. In some cases, the physician uses a separate single metal blade for pressing on the anterior and posterior walls of the vagina cavity. Thus, the examination involves the use of several tools, as well as assembling and disassembling operations. Thus, it is impossible with conventional specula to conduct more concentrated and localized measurements for determining position and severity of vaginal prolapses or conduct examination of one wall of the vaginal cavity without removing the entire speculum from the vagina.

Objects of the Invention

It is an object of the present invention to provide a method for determining positions and severity of vaginal prolapses solely with the use of a vaginal speculum, without completely removing the vaginal speculum from the patient's vagina and without the use of additional instruments. Another object is to provide the aforementioned method wherein vaginal measurements are performed by manipulating with sliding removable blades having measurement scales on their surfaces.

SUMMARY OF THE INVENTION

A method for measuring positions and severity of vaginal prolapses or for performing other vaginal measurements associated with urological and gynecological procedures is based on the use of a vaginal speculum with sliding removable blades. The blades are guided in two parts pivotally interconnected through a fork-like member so that the blades can be expanded and fixed in an expanded state in order to dilate the vagina for observing the condition of the vagina cavity. The blades and the guiding parts are made of a transparent material, and the blades have measurement scales on their surfaces. The blades can be partially or completely removed for replacement with blades of other dimensions without withdrawing the entire speculum from the vagina. Various measurements, such as determining the length of the vagina or determining positions and severity of the vaginal prolapses, are performed by manipulating with the removable blades and the speculum as a whole and calculating target dimensions by using data read from the scales. Provision of retractable blades makes it possible for a physician to withdraw the blades in an alternating sequence for exposing one of the walls of the vagina cavity by pressing down with the longer blade on the opposite wall.

DETAILED DESCRIPTION OF THE INVENTION

For better understanding the method of the invention, it would be advantageous first to understand the construction of vaginal specula suitable for realization of the aforementioned method. Such specula are disclosed in U.S. patent application Ser. No. 09/565,613 which was filed by the same applicants on Apr. 05, 2001 and for which a notice of allowance has been issued.

Figures 1, 2:
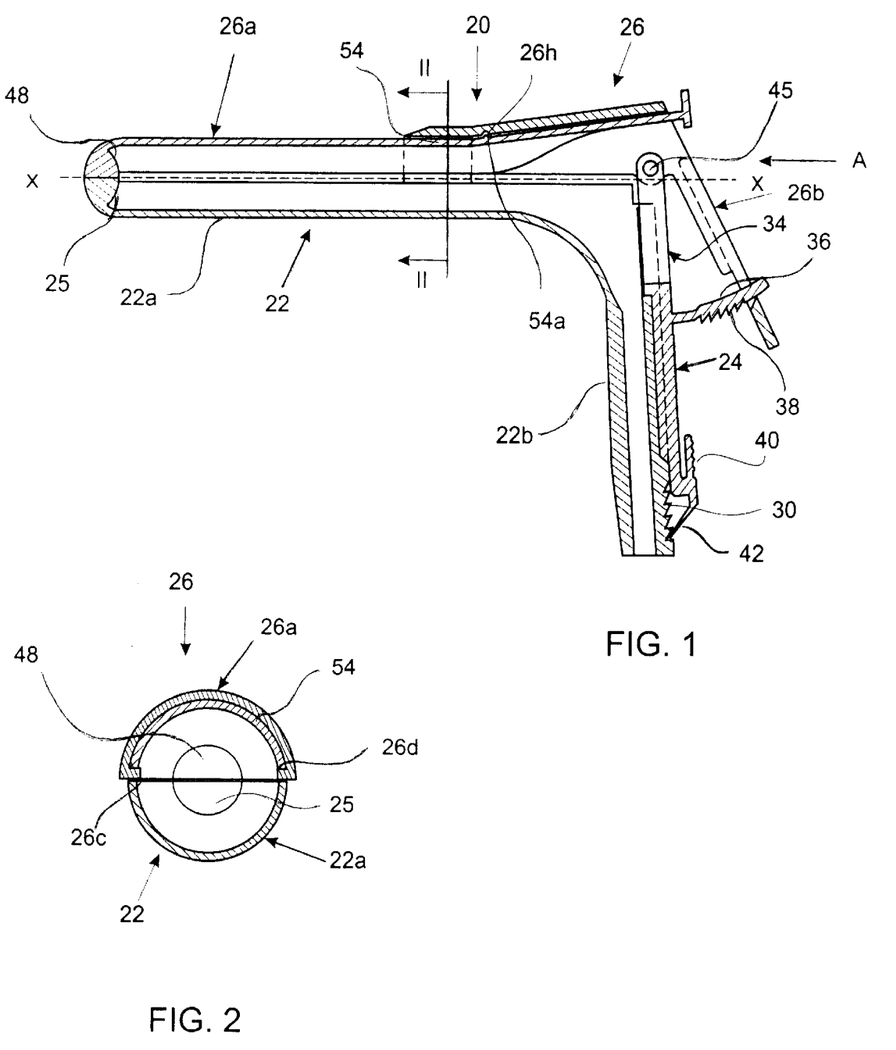
FIG. 1 is a side sectional elevation view of the speculum for carrying out the method of the invention.
FIG. 2 is a sectional view along line II—II in FIG. 1.

As can be seen from FIG. 1, which is a side elevation view of the speculum 20 suitable for the method of the invention, the speculum 20 comprises a fixed blade member 22, a slide member 24, and a movable blade member 26.

Figures 3, 4:
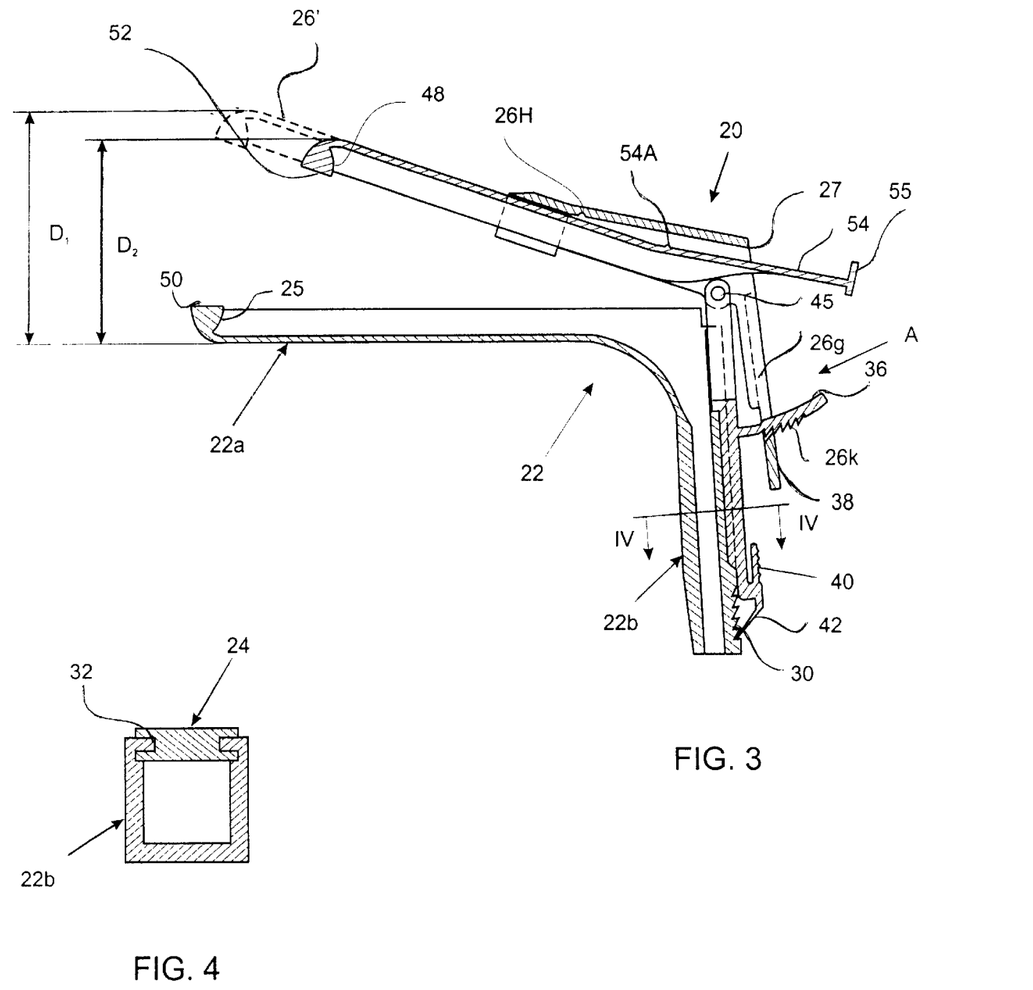
FIG. 3 is a view of the vaginal speculum of FIG. 1, which shows the blades of the speculum in an open or expanded position.
FIG. 4 is a sectional view along line IV—IV in FIG. 3.

The fixed blade member 22 has an L-shaped configuration with a blade portion 22a insertable into the patient's vagina, and a handle portion 22b substantially perpendicular to the blade portion 22a. The blade portion 22a is hollow and, as can be seen from FIG. 2, which is a sectional view along line II—II in FIG. 1, it has a semicircular cross-section. The distal end of the blade portion 22a, i.e., the end opposite to the handle portion 22a, has a half-lens 25, which is formed, e.g., molded, integrally with the remaining part of the blade portion 22a. The half-lens 25, in fact, is a portion of a biconvex lens obtained by cutting a lens by half along an optical axis X—X (FIG. 1). FIG. 3 is a view of the vaginal speculum 20 of the invention, which shows the blades of the speculum of FIG. 1 in an open or expanded position.

Ratchet teeth 30 are formed on the lower rear side of the handle portion 22b for the purposes explained later. As shown in FIG. 4, which is a sectional view along line IV—IV in FIG. 3, the part of the handle portion 22a located above the teeth 30 may have a slot 32 of a T-shaped cross-section for guiding a complementary shaped part of the slide member 24, which also has a T-shaped cross-section.

The slide member 24 of the vaginal speculum 20 of the present invention has a fork-like straight portion 34, a rearward projection 36 which is substantially perpendicular to the straight portion 34 and has teeth 38 on one of its sides, and a tail portion 40 with a pawl 42 for engagement with ratchet teeth 30.

Figure 5:
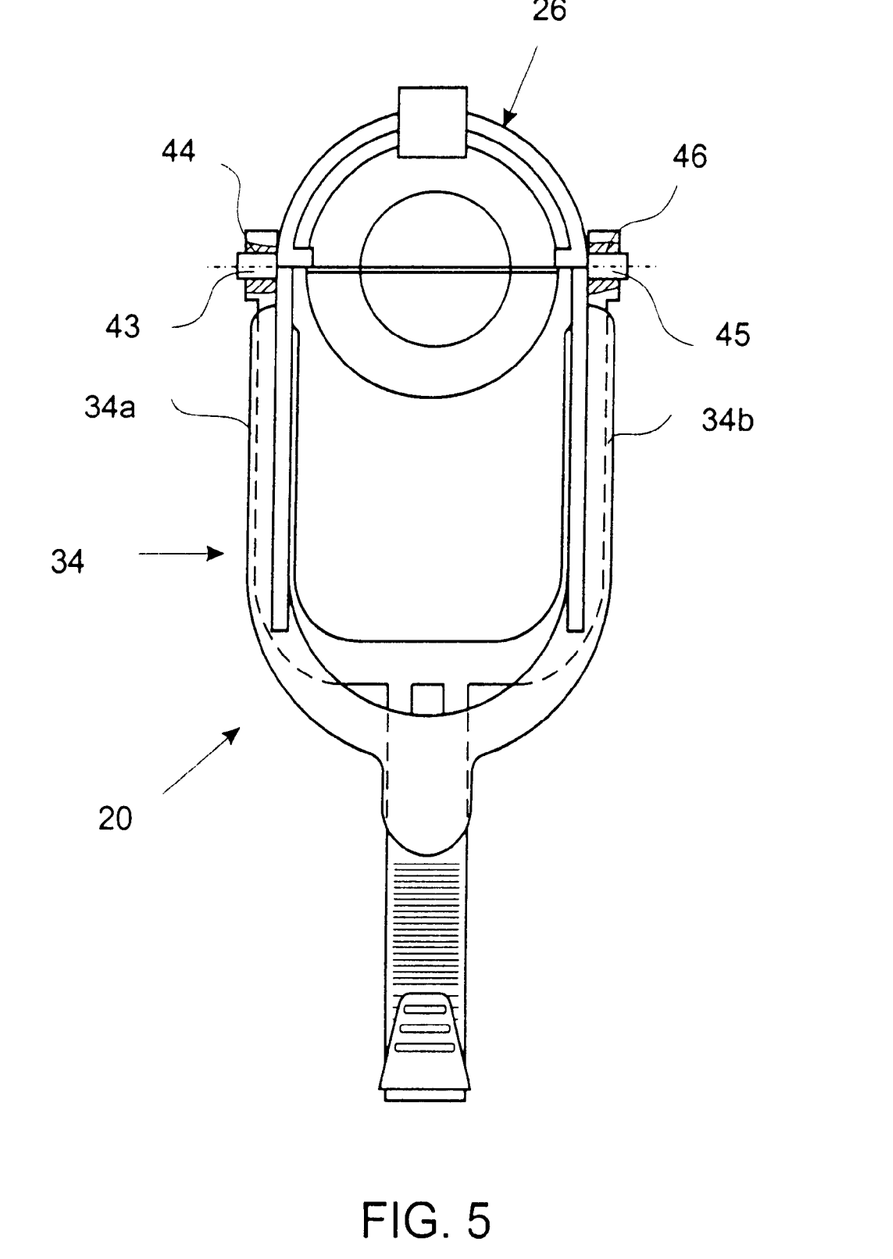
FIG. 5 is a rear view of the vaginal speculum of the invention in the direction of arrow A in FIG. 1.

FIG. 5 is a rear view of the vaginal speculum 20 of the invention in the direction of arrow A in FIG. 1. As can be seen from FIG. 5, the fork-like portion 34 of the slide has holes 44 and 46 on the inner sides of fork legs 34a and 34b. These holes receive projections 43 and 45 formed on the outer side walls of proximal part of the movable member 26. As a result, the movable member 26 can perform rotating or swinging movements around projections 43 and 45 as pivot points.

Similar to the fixed member 22, the movable member 26 has an L-shaped configuration (FIG. 1) with a blade portion 26a insertable into the patient's vagina and a trigger portion 26b formed on the proximal end of the speculum and oriented substantially perpendicular to the blade portion 26a. The insertable blade portion 26a of the moveable member 26 is symmetrical to the insertable blade portion 22a of the fixed member 22 and is complementary thereto so that in a closed state of the speculum 20 shown in FIG. 1 both blade portions form a substantially round cross section. In other words, the blade portion 26 has a semicircular or oval cross-section shown in FIG. 2 and has a half-lens 48 with a flat surface 50 (FIG. 3). Thus, as shown in FIG. 1, in a closed state of the speculum, the blade portions 22 and 26 form a tubular body of a complete round or oval cross-section with a complete biconvex lens formed by two half-lenses 25 and 48 at the distal end of the speculum. Reference numeral 52 designates a flat surface on the lens portion 48.

As shown in FIG. 2, in the embodiment shown in FIGS. 1 through 5, the movable blade member 26 has, on the inner side, guide edges 26c and 26d. As shown in FIG. 1, guide edges 26c and 26d may be formed only on a short portion (L) of the entire length of the movable member 26. The guide edges 26c and 26d are used for slidingly guiding a removable blade 54 (FIGS. 1, 2, and 3) of the moveable member 26. In other words, moveable member 26, in turn, consists of two parts, i.e., the main part with the trigger portion 26b and the adjustable blade 54, which contains the aforementioned insertable part 26a. The adjustable blade 54 may have tight sliding fit in the guide portion formed by edges 26c and 26d, so that it can be shifted in the rearward direction, i.e., in the direction opposite to the direction of arrow A in FIG. 1, to assume a position shown in FIG. 3. For convenience of shifting, the adjustable blade 54 may have a tab 55 on its rear end. Thus, after the adjustable blade 54 has been shifted in the rearward direction, it will be held in the adjusted position by the aforementioned tight fit. Furthermore, as shown in FIG. 3, in this case the expansion diameter D2 will be smaller than the expansion diameter D1 for non-adjustable blade member 26 shown in FIG. 3 by the broken line 26'.

In order to prevent the adjustable blade 54 from sliding relative to moveable member 26 during insertion of the speculum into the patient's vagina, the proximal end of the adjustable blade 54 has a dent 54a on its outer surface, whereas the moveable portion 26 has an indent 26h on its inner surface for engagement with the dent 54a. Normally the dent 54a is engaged with the indent 26h under the effect of resiliency of the adjustable blade 54, so that during insertion of the distal end of the speculum 20 into the patient's vagina the adjustable blade will not slide relative the moveable portion. In addition, during insertion the tab 55 will bears up against the thumb of a physician who inserts the speculum. In order to adjust the position of the adjustable blade 54 and thus to move it relative to the moveable portion 26, it is necessary to slightly push the proximal end of the adjustable blade 54 down in order to disengage the indent 26h from the dent 54a and then to move the adjustable blade 54a in a required direction.

As shown in FIG. 1, trigger portion 26b has an opening 26g with teeth 26k on the solid part of the trigger 26b for engagement with the teeth 38 on the projection 36 (FIG. 1). The teeth 26k and 38 may be formed as ratchet teeth and a pawl so that pushing on the trigger 26 in the direction of arrow A will rotate the movable member 26 on pivot projections 43 and 45 for expanding the speculum blades 22 and 26. Due to the ratchet engagement between the teeth 26k and 38, after the trigger is releases, the blades 22 and 26 will remain in the expanded position shown in FIG. 3.

The adjustable blade 54 can be completely removed and replaced by another blade having a different length.

If necessary, in addition to the movement of the adjustable blade 54 in the axial direction of the speculum 20, another adjustment can be carried out by guiding the sliding member 24 in guide grooves 32 (FIG. 4), thus raising or lowering the pivot projections 43 and 45 together with the movable member 26 with respect to the fixed member 22. This allows expanding the adjustment range.

Figure 6:
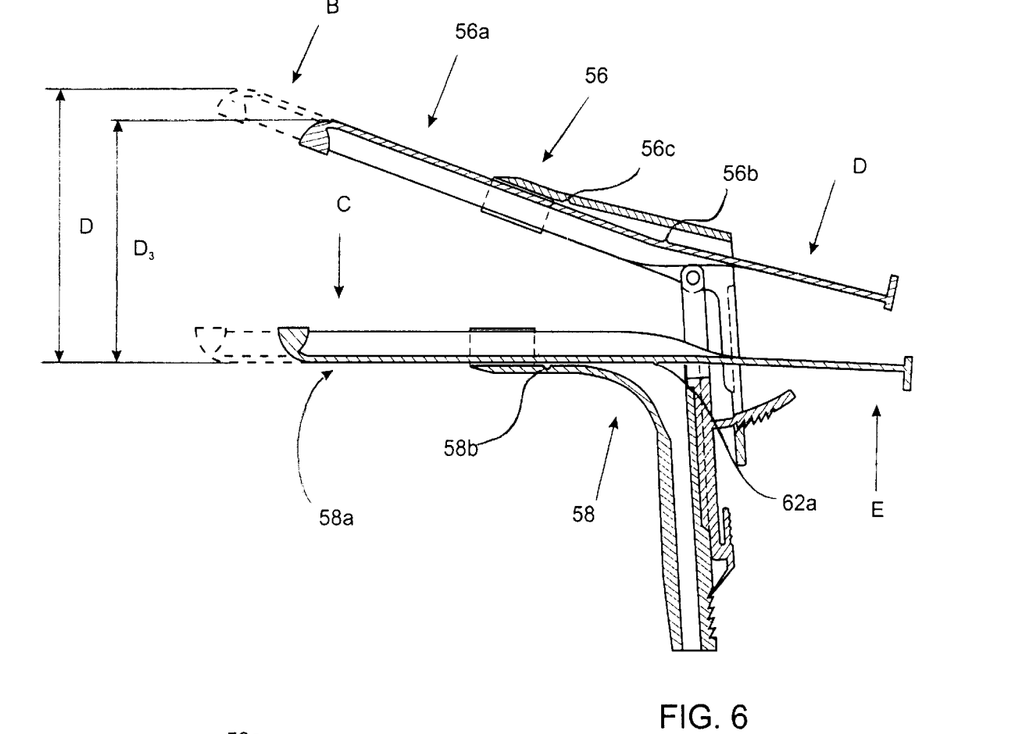
FIG. 6 is a side sectional elevation view of the speculum according to another embodiment of the invention, in which both blades are adjustable.
Figure 7:
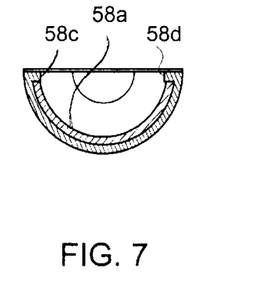
FIG. 7 is a sectional view along line VII—VII in FIG. 6.

FIG. 6 illustrates another embodiment of the vaginal speculum of the invention, in which both blades, i.e., a blade 56a of a movable member 56 and a blade 58a of a fixed member 58 are adjustable. The rest of the construction is the same as in the embodiment shown in FIGS. 1 through 5. As shown in FIG. 7, which is a sectional view along line VII—VII in FIG. 6, the fixed member 58 has on the inner side of the blade portion 58a, guide edges 58c and 58d. As shown in FIG. 6, guide edges 58c and 58d may be formed only on a short portion ($L_1$) of the entire length of the fixed member 58. The edges 58c and 58d are used for slidingly guiding the adjustable blade 58a (FIG. 6) of the fixed member 58. The speculum of FIG. 6 makes it possible to adjust the positions of both adjustable blades 56a and 58a, so that along with the significant decrease in the diameter $D_3$ (FIG. 6), it becomes possible to ensure painless partial withdrawal of the of the blades in an expanded state for observation of the proximal part of the vagina.

In order to prevent the adjustable blade 58a from sliding relative to fixed member 58 during insertion of the speculum into the patient's vagina, the proximal end of the adjustable blade 58a has a dent 62a on its outer surface, whereas the fixed member 58 has an indent 58b on its inner surface for engagement with the dent 62a.

The construction of the dent 56b and the indent 56c in the upper adjustable blade 56a and the moveable portion 56 are the same as in the moveable part 26 and in the adjustable blade 54 of the embodiment of FIG. 1.

Figure 8:
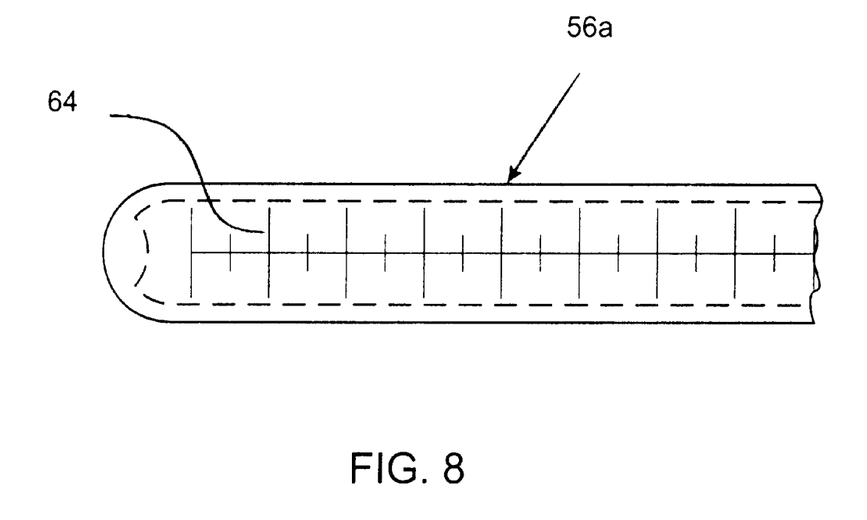
FIG. 8 is a view in the direction of arrow B in FIG. 6.
Figure 9:
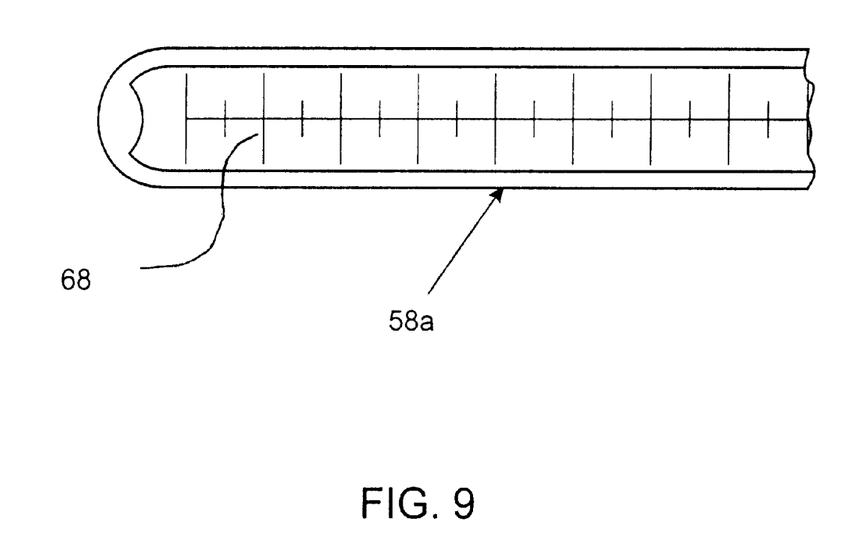
FIG. 9 is a view in the direction of arrow C in FIG. 6.

The vaginal speculum of the present invention is additionally provided with means for locating a position of a vaginal prolapse, of both cystocele-type and rectocele type. For locating a position of the aforementioned prolapses, both adjustable blades have on their proximal ends scales, e.g., in centimeters. FIGS. 8 and 9 are fragmental views in the direction of arrows B and C of FIG. 6, respectively. As can be seen from these drawings, the adjustable blade 56a has a scale 64 with divisions applied onto its outer surface and has the very end as a zero or a reference point with the number in centimeters or inches increased from this point to the proximal end. In other words, the scale 64 can be used as a conventional ruler. Similarly, a scale 68 has divisions applied onto the inner surface of the blade 58a. The divisions should be made black so that they could be seen on the transparent background of the material of the adjustable blades 56a and 58a. The lower scale also has its reference point at the outermost distal point of the adjustable blade 58a.

Figure 10:
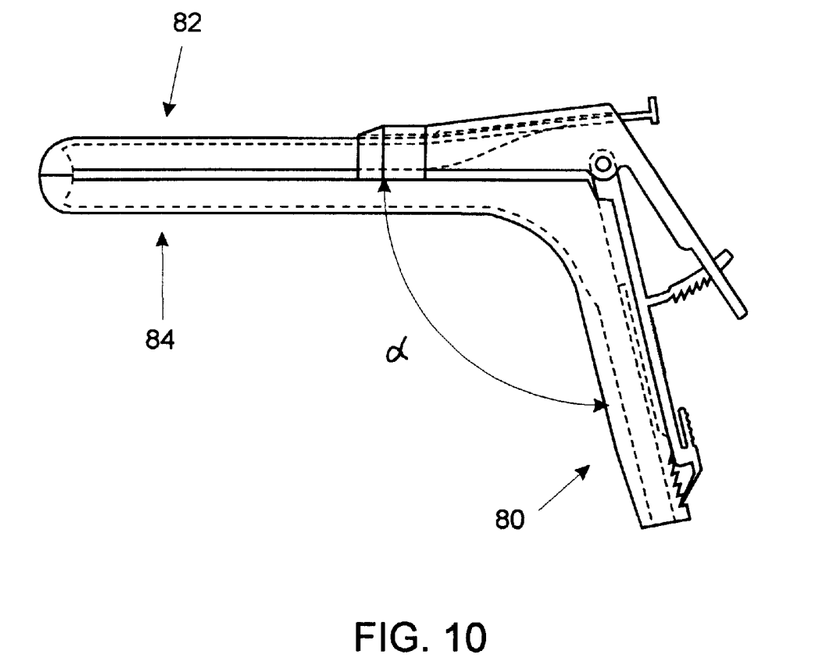
FIG. 10 illustrates another embodiment of the speculum of the invention in which the handle portion is bent backward to form an obtuse angle with the longitudinal direction of the adjustable blades.

FIG. 10 shows another embodiment of the speculum of the invention in which the handle portion 80 can be bent backward to form an obtuse angle α with the longitudinal direction of the adjustable blades 82 and 84 in order not to interfere with outwardly extending parts of the patient's body, such as buttocks, e.g. in overweight women.

Figure 11:
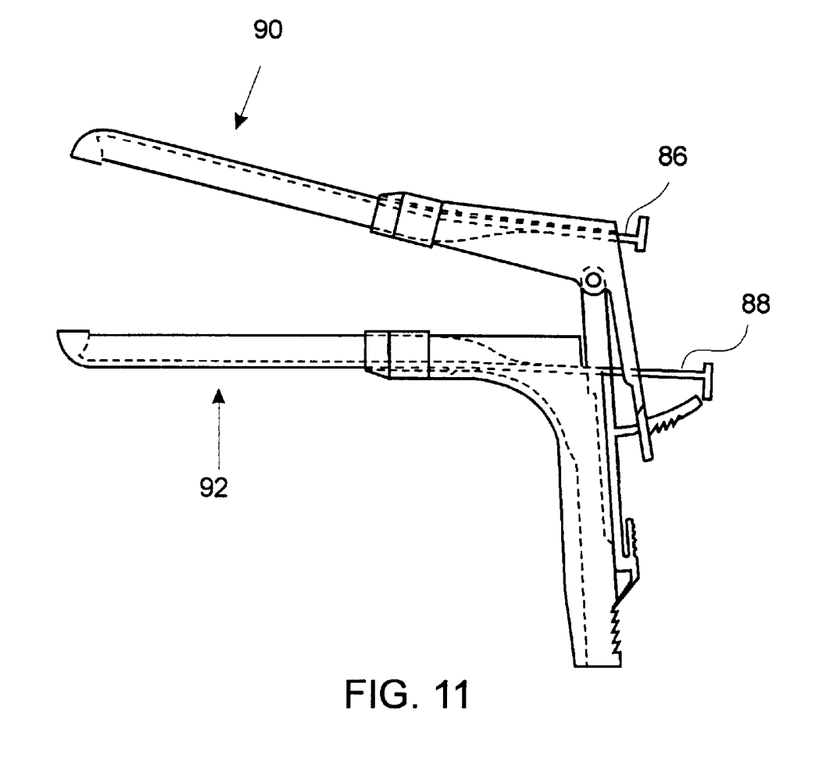
FIG. 11 shows another embodiment of the speculum of the invention in which the proximal ends of the adjustable blades are bent radially outward from the longitudinal axis of the adjustable blades.

FIG. 11 shows another embodiment of the speculum of the invention in which the proximal ends 86 and 88 of the adjustable blades 90 and 92 are bent radially outward from the longitudinal axis of the adjustable blades 90 and 92. This is necessary in order not to obscure the vision through the central opening of the speculum when, during expansion of the distal ends of the blades 90 and 92, their proximal ends 86 and 88 move radially inwardly toward each other.

Figure 12:
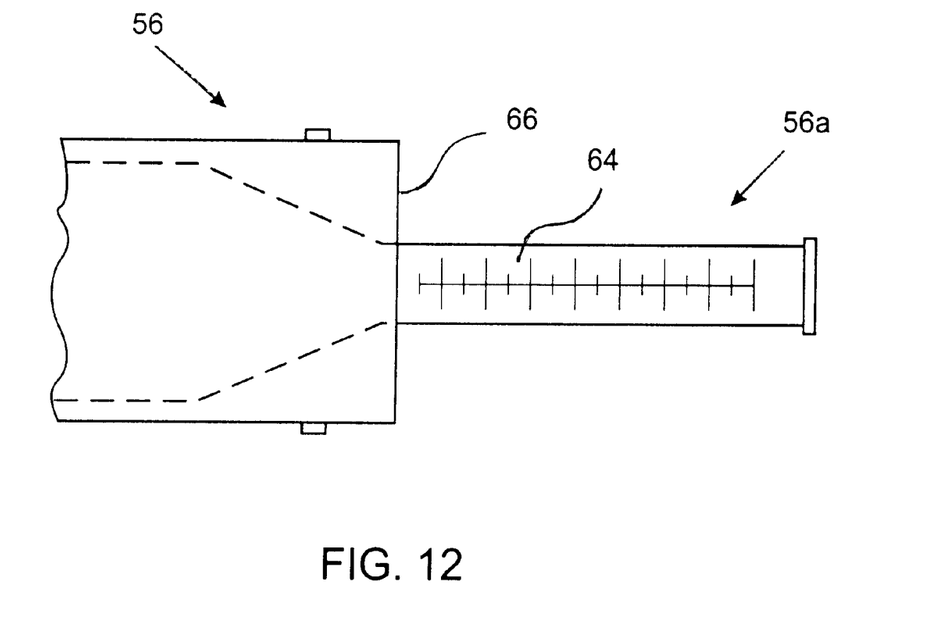
FIGS. 12 and 13 are fragmental views in the direction of arrows D and E of FIG. 6, respectively.
Figure 13:
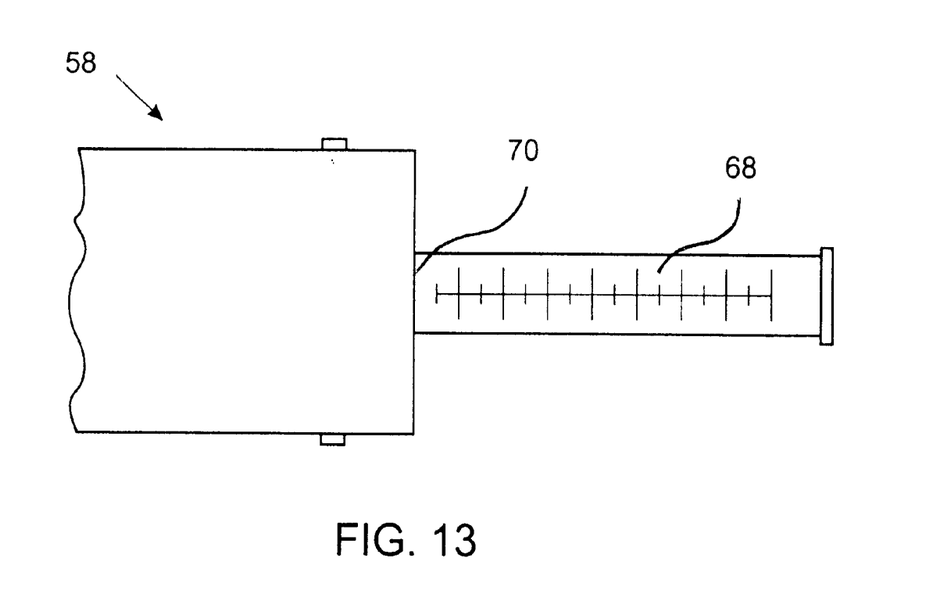

FIGS. 12 and 13 are fragmental views in the direction of arrows D and E of FIG. 6, respectively. As can be seen from these drawings, the scale 64 on the movable or adjustable blade 56a may extend further to the protruding proximal end 60 of the adjustable blade 56a, so that measurements can be read with regard to the rear edge 66 of the movable part 56. The same principle can applied to the fixed member 58, where divisions of the scale 68 can extend to the protruding proximal end 72 (FIG. 13), so that measurements can be read with regard to the rear edge 70 of the fixed member 58.

Procedure for the Use of the Retractable Vaginal Speculum

The procedure is started from inspection of the vaginal introitus to determine the status of the vaginal skin, the size of the vaginal outlet, and the presence or absence of pelvic organ prolapse. A retractable vaginal speculum of a required size is then chosen.

Since a retractable vaginal speculum is normally a disposable instrument, which is sterilized and packed into a sealed package, it is unpacked and removed from the package. In the case of the speculum of FIGS. 1 through 5, the insertable ends 26a and 22a of the blade members 22 and 26 are then lubricated using a water-soluble lubricant. The insertable ends 26a and 22a of the speculum 20, are then gently inserted into the vaginal canal in a closed state of the speculum 20 shown in FIG. 1, and are advanced all the way to the vaginal vault or at the level of the uterine cervix 101, shown in FIG. 14, which is a sectional view of normal reproductive organs of a woman.

The physician first visually observes the condition of the uterus cervix through the optical lens formed by semilenses 48 and 25. The purpose of this observation is to detect initial changes on the cervix that could not be detected by a naked eye. Such changes may be initial erosion, papilomas, etc.

The speculum 20 is then opened by moving the blade members 22 and 26 apart to further visualize the vaginal vault or the cervix. This is done by pushing on the trigger portion 26b so that the teeth 26k slide in a ratchet manner over the teeth 38 of the projection 36. As a result, the blade members 22 and 26 of the speculum assume the positions shown in FIG. 3 and thus expand the vaginal cavity (not shown in the drawings).

The physician can then observe the appearance of the vaginal mucosa at the level of the vault, or observe the appearance of the cervix. If necessary, the length of the vaginal canal is measured from the vaginal vault or the posterior aspect of the cervico-vaginal junction to the level of the hymenal line. This is achieved by pushing down on the tab 55 of the adjustable blade 54 for disengaging the dent 54a from the indent 26h and by moving the adjustable blade 54 to a required position. Measurement is made by reading the numbers of the scale 64 with regard to the hymeneal line, as will be described later. As shown in FIGS. 8 and 9, where FIG. 8 is a view in the direction of arrow B, and FIG. 9 is a view in the direction of arrow C in FIG. 6, the divisions of the scale are applied onto the entire length of the blades 54 and 25 in the embodiment of FIG. 1, and of the blades 54a and 58a in the embodiment of FIG. 6, so that the physician could measure the distance from the hymeneal ring to the cervix, as well as the distance to the end of the prolapse using the very end of the distal end as the reference point for measurement. If necessary, the physician performs paps smear and/or collection of fluids for culture and or cytology as indicated. Slight thickening of the curved end walls on the distal ends of the blades 20 and 22 caused by the formation of semilenses does not create any obstacles for this operation.

For separate observation of the condition of one of the walls of the vagina, the adjustable blade, e.g. blade 54 (FIGS. 1 and 2) is then retracted halfway so that the blade of the speculum 20 (or speculum 56) is in a position required for the observation of the exposed wall. Since one of the blades, i.e., the blade 22 remain in the initial position (FIG. 3) and another blade, i.e., 26, is partially withdrawn, the physician may observe the condition of the exposed part of the vagina wall for observation and thus to see prolapses on the exposed wall. This would be unattainable for the conventional speculum without completely withdrawing the entire speculum, disassembling it, and using only one part as a spade for pressing on one wall of the vagina in order to expose the opposite wall for observation. In the case of the embodiment of FIG. 6, both adjustable blades 56a and 58a can be withdrawn in alternating sequence, or can be retracted both together to see if the uterus or the vaginal vault (dome) will drop further down. The degree of the drop of the uterus or the vaginal vault (dome)(if the uterus is gone) in relation to the hymeneal line can be measured with the calibrated retractable blade. This is easily done by positioning the tip of the sliding blade to the lowest edge of the prolapsing organ, i.e. cervix or vaginal vault or cystocele or rectocele and measuring from that distance to the level of the hymeneal line.

Figures 14, 15:
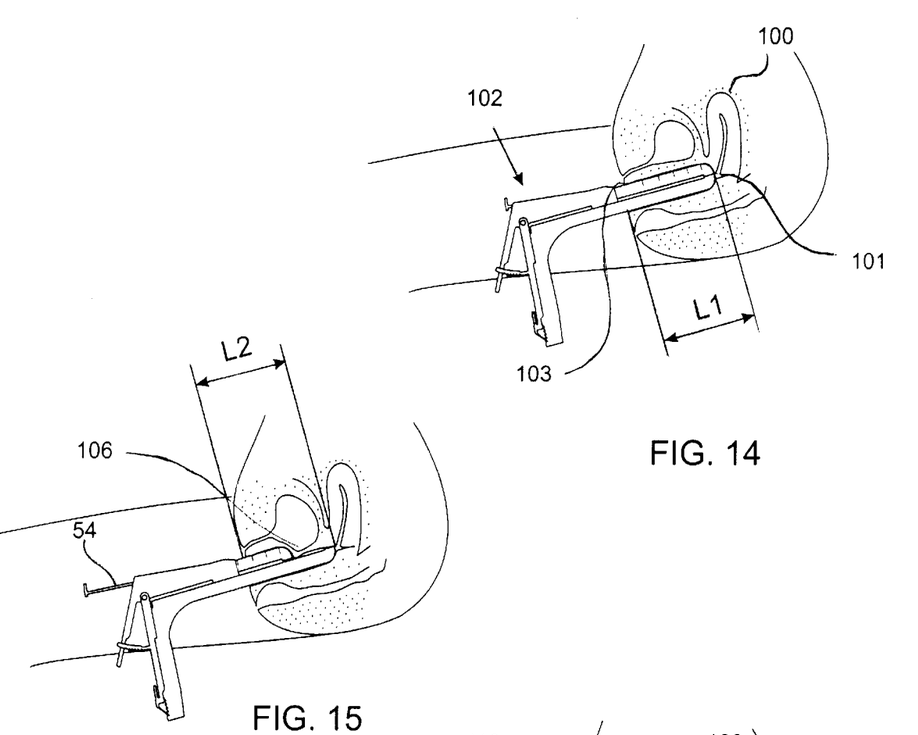
FIG. 14 is a sectional view of normal reproductive organs of a woman.
FIG. 15 shows an example of cystocele inside the vaginal canal.
Figure 16:
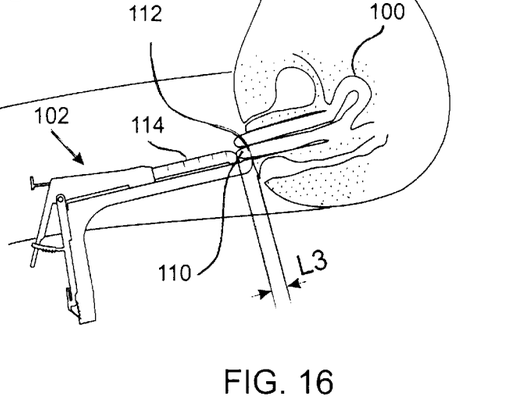
FIG. 16 shows a condition of a cystocele protruding outside the vagina.

The aforementioned measuring procedure will be now explained with reference to FIGS. 14, 15, and 16; wherein FIG. 12 shows a normal anatomy of female reproductive organs, FIG. 15 shows an example of cystocele inside the vaginal canal and method for measuring its position and dimensions, and FIG. 16 shows a condition of a cystocele protruding outside the vagina and a method for measuring the length of this cystocele.

As shown in FIG. 14, the distance L between the tip of the cervix 100 and the hymeneal ring is measured by inserting the speculum 102 in a closed state shown in FIG. 1 to contact with the dome of the uterus 100 and by reading the number on the scales of the blades at the hymeneal line 104. The distance between these two points will be in centimeters and will be recorded as a minus number. For example, if the cervix is prolapsing (not shown) and the distance between the edge of the cervix inside the vaginal canal to the hymeneal ring is 3 centimeters, then the cervix prolapse is −3 cm. Likewise, if, as shown in FIG. 15, there is a cystocele 106 and it is prolapsing or dropping, the physician can retract the adjustable blade 54 (FIG. 3), or the adjustable blade 56a (FIG. 6), and then move it to contact of the distal tip of this adjustable blade with the edge of the systole. The distance L1 between with the edge of the cystocele 106, touching the tip of the retractable blade 106, and the level of the hymeneal line 108 is then measured with regard to the hymeneal line 104 as a reference point. If L1 is 4 centimeters, then the prolapsing cystocele is −4 cm. The same procedure can be performed with regard to rectocele (not shown) by moving the adjustable blade 58a (FIG. 6).

If the prolapse is so severe that, as shown in FIG. 16, it is coming out of the vaginal opening which can be observed even before the speculum is inserted or after the speculum is completely removed and the organ prolapsing; for example, the cystocele 110 is protruding out, then the measurement of the prolapse will be a distance L2 from the hymeneal line 112 to the furthest tip of the prolapsing cystocele. This distance is measured by means of the scale on the tip 114 of the speculum 116 as by a conventional ruler.

If the prolapse is dropping outside the hymeneal line; i.e. is 5 centimeters, the cystocele prolapse is +5 cm.

In accordance with an alternative method, the severity and positions of the prolapses can be measured by using rear edges 66 (FIG. 12) and 70 (FIG. 13) of respective proximal portions of the blades. In this case, the distance L1 can be measured by reading the number on the scale 68 between the edge 70 of the cystocele 106 touching the tip of the retractable blade 106 and between the edge 70 and the hymeneal line 108. The length L1 will be determined by subtracting the second reading from the first one. The same is applicable for measuring rectocele (not shown).

Thus it has been shown that the invention provides a method for determining positions and severity of vaginal prolapses solely with the use of a vaginal speculum, without completely removing the vaginal speculum from the patient's vagina and without the use of additional instruments. The method is performed by manipulating with sliding removable blades having measurement scales on their surfaces.

Although the invention has been shown and described with reference to specific embodiments, it is understood that these embodiments should not be construed as limiting the application of the invention, so that any changes and modifications are possible, provided they do not depart from the scope of the patent claims. For example, measurements described in the specification can be made with a vaginal speculum, in which a simple sliding ruler is used instead of a scaled removable blade. In such a speculum, the ruler can slide along the guides formed on the inner surface of the conventional non-adjustable blade.

What is claimed is:

1. A method for measuring positions and dimensions of vaginal prolapses comprising the steps of:

providing a vaginal speculum having a first member with a proximal part and a distal part arranged in a longitudinal direction, a second member slidingly attached to said proximal part for moving in a direction transverse to said longitudinal direction, said second member having means for fixing thereof to said proximal part of said first member, and a third member having a proximal part and a distal part arranged in a longitudinal direction, said third member being pivotally connected to said second member for rotation with respect to said first member when said second member is moved in said direction transverse to said longitudinal direction, at least one of said first and third members having said distal part in the form of a completely removable element moveable in said longitudinal direction, said speculum having a closed state when said first and third members are in contact with each other and an expanded state when said first and third members are spread apart under effect of said rotation;

providing a scale on said completely removable element;

selecting a reference point on a patient's body or on said speculum for reading the numbers on said scale with respect to said reference point;

inserting said vaginal speculum in said closed state into the vagina of a female patient until contact with the top of the cervix;

reading the number on said scale and determining the distance L1 from said reference point to said top of the cervix;

withdrawing said completely removable element in a direction away from the cervix;

expanding said speculum due to said rotation thus exposing the wall of the vagina on the side of said completely removable element for observation;

observing a prolapse on said wall of the vagina and visually determining its severity;

moving said completely removable element to the tip of said prolapse;

reading the number on said scale and determining the distance L2 from said reference point to said tip of said prolapse;

subtracting L2 from L1, thus determining the position of said prolapse.

2. The method of claim 1, further comprising the step of defining the position of said prolapse as a distance from said tip of said prolapse to the hymeneal line and assigning to said distance L1 a negative value if the prolapse is inside the vagina and a positive value if the prolapse protrudes from the vagina beyond the hymeneal line.

3. The method of claim 2, wherein said completely removable element is a removable blade.

4. A method for measuring positions and dimensions of vaginal prolapses comprising the steps of:

providing a vaginal speculum having a first member with a proximal part and a distal part arranged in a longitudinal direction, a second member slidingly attached to said proximal part for moving in a direction transverse to said longitudinal direction, said second member having means for fixing thereof to said proximal part of said first member, and a third member having a proximal part and a distal part arranged in a longitudinal direction, said third member being pivotally connected to said second member for rotation with respect to said first member when said second member is moved in said direction transverse to said longitudinal direction, said first member having said distal part in the form of a first completely removable element moveable in said longitudinal direction, said third member having said distal part in the form of a second completely removable element moveable in said longitudinal direction, said speculum having a closed state when said first and third members are in contact with each other and an expanded state when said first and third members are spread apart under effect of said rotation;

providing a first scale and a second scale on said first completely removable element and on said second completely removable element, respectively;

selecting a reference point on a patient's body or on said speculum for reading the numbers on said first scale and on said second scale with respect to said reference point;

inserting said vaginal speculum in said closed state into the vagina of a female patient until contact with the top of the cervix;

reading the number on said first scale or said second scale and determining the distance L1 from said reference point to said top of the cervix;

withdrawing one of said completely removable elements in a direction away from the cervix;

expanding said speculum due to said rotation thus exposing the wall of the vagina on the side of said completely removable element for observation;

observing a prolapse on said wall of the vagina and visually determining its severity;

moving said completely removable element to the tip of said prolapse;

reading the number on said scale and determining the distance L2 from said reference point to said tip of said prolapse;

subtracting L2 from L1, thus determining the position of said prolapse.

5. The method of claim 4, further comprising the step of observing the prolapses on the opposite side of the vagina wall by repeating the steps of withdrawing, expanding, observing, moving, and subtracting for the second completely removable element.

6. The method of claim 5, further comprising the step of defining the position of said prolapse as a distance from said tip of said prolapse to the hymeneal line and assigning to said distance L1 a negative value if the prolapse is inside the vagina and a positive value if the prolapse protrudes from the vagina beyond the hymeneal line.

7. The method of claim 5, wherein said completely removable element is a removable blade.

* * * * *